United States Patent [19]

Mentrup Edgar et al.

[11] Patent Number: 5,498,420
[45] Date of Patent: Mar. 12, 1996

[54] STABLE SMALL PARTICLE LIPOSOME PREPARATIONS, THEIR PRODUCTION AND USE IN TOPICAL COSMETIC, AND PHARMACEUTICAL COMPOSITIONS

[75] Inventors: Mentrup Edgar, Frankfurt; Christoph Michel, Obertshausen; Thomas Purmann, Aschaffenburg, all of Germany

[73] Assignee: Merz & Co. GmbH & Co., Frankfurt am Main, Germany

[21] Appl. No.: 430,687

[22] Filed: Apr. 27, 1995

Related U.S. Application Data

[63] Continuation of Ser. No. 133,674, Oct. 8, 1993, abandoned, which is a continuation-in-part of Ser. No. 863,989, Apr. 6, 1992, abandoned.

[30] Foreign Application Priority Data

Apr. 12, 1991 [DE] Germany ............... 41 11 982.7

[51] Int. Cl.$^6$ ................................................. A61K 9/127
[52] U.S. Cl. ........................................... 424/450; 424/401
[58] Field of Search .................................. 424/450, 401; 428/402.2

[56] References Cited

U.S. PATENT DOCUMENTS

| | | | |
|---|---|---|---|
| 4,508,703 | 4/1985 | Redziniak | 424/450 |
| 5,008,109 | 4/1991 | Tin | 424/422 |

FOREIGN PATENT DOCUMENTS

| | | |
|---|---|---|
| 3125953 | 1/1982 | Germany . |
| 3713493 | 10/1987 | Germany . |
| 2166107 | 4/1986 | United Kingdom . |
| 2226002 | 6/1990 | United Kingdom . |

OTHER PUBLICATIONS

USP XXII, NF XVII, cover sheet, index p. v, and pp. 1942 and 1943 relating to lecithin, by USPC, Inc. (1989)—four (4) pages.
Chemical Abstracts Service, Registry Handbook, cover page plus page 2478RG with registry No. 68458-51-5 (1978 Supplement) by CAS (1978)—two (2) pages.
JP-Z: Pat. Abstr. Japan C-721, May 23, 1990, vol. 14/No. 242 (JP 2-63548A).

*Primary Examiner*—Gollamudi S. Kishore
*Attorney, Agent, or Firm*—Gordon W. Hueschen

[57] ABSTRACT

The invention relates to liposome preparations with controllable vesicle size and type between about 20 and 150 nm and high stability without increased permeability, the vesicle membrane of the liposomes consisting essentially of lecithin and 10%–90%, preferably 16–90%, and most especially 20–80%, of a specified fatty acid-esterified collagen hydrolysate (FAECH), namely, a fatty acid ester of a lipoaminoacid or lipopeptide, representatively OHAP, plus traditional jellifying agents, adjuvants, and pharmaceutical agents as desired, and the production and use thereof in cosmetic and pharmaceutical compositions, as well as a method of controlling vesicle dimensions and reducing vesicle particle size by employing increased and previously believed inoperative ratios of FAECH to lecithin.

18 Claims, No Drawings

STABLE SMALL PARTICLE LIPOSOME PREPARATIONS, THEIR PRODUCTION AND USE IN TOPICAL COSMETIC, AND PHARMACEUTICAL COMPOSITIONS

The present application is a continuation of our prior-filed application Ser. No. 08/133,674, filed Oct. 8, 1993, now abandoned, which in turn is a continuation-in-part of our prior-filed application Ser. No. 07/863,989, filed Apr. 6, 1992, now abandoned.

BACKGROUND OF THE INVENTION

1. Field of Invention

Small-size essentially impermeable liposomes containing lecithin (a), which are dimensionally stable and non-aggregating, and the size of which is controlled and determined by the fatty acid-esterified lipoamino acid or lipopeptide (b) content thereof, their production, and their use, the liposome membranes consisting essentially of (a) and (b).

2. Prior Art

As is generally known, liposomes are small vesicles having a bilayer structure. They are used in the pharmaceutical area as drug vehicles, e.g., for parenteral or topical application.

The most varied agents with different chemico-physical properties can be incorporated into liposomes. Water-soluble agents can be located in the core and between the vesicle bilayers. Lipophilic substances, on the contrary, are incorporated in the bilayer. Therefore, the incorporation of substantial amounts of such agents into liposomes can result in a marked increase in vesicular diameter. In such case, pharmacokinetics and therefore also therapeutic properties can change considerably. Small liposomes afford more advantages because they are not identified by the RES (reticulo-endothelial system). In consequence, they are not eliminated from circulation through hepatic or renal filtration, resulting in higher plasma levels over prolonged periods of time. For example, for such small liposomes half-lives of over 20 hours were determined (cf. J. Senior et al., Biochem. Biophys. Acta 839, 1 (1985)). This means greater availability of an encapsulated active agent at the potential site of action, e.g., a tumor, because the circulating liposome deposit is very slowly degraded by enzymatic decomposition and interaction with other blood constituents. During this process the encapsulated active substance is released and is available for therapeutic utilization.

Large vesicles, on the contrary, are identified by the RES (hepatic Kupffer cells) as foreign bodies and destroyed. Even a few minutes after the i.v. application of such particles, 90% of the particles are eliminated. With the application of 400 nm liposomes, a half-life of about 10 min. was found; with particles of 1000 nm it was reduced to only about 5 min (cf. J. Senior et al. and P. O. Lelkes, Liposome Technology, Vol. 1). Also after topical application, small vesicles containing active ingredients may exert a better effect through improved penetration, for example, along the hair follicles. Additionally, an interaction may be possible with the natural bilayer structures in the intercellular gaps (cf. W. Curatolo, Pharm. Res. 4, 271–341 (1987), G. Grubauer et al., J. Lipid Res. 30, 89–96 (1989)). Furthermore, from a statistical point of view, the interaction of small unilamellar vesicles (SUV) with other cells is likely to be greater than that of multilamellar vesicles (MLV), which facilitates the transfer of membrane constituents, e.g., bilayer-bound ingredients.

In FR-A 2 591 105, pharmaceutical compositions based on lipid-containing multilamellar vesicles for dermatological or cosmetic application are described which contain a retinoid or an analogue thereof. This combination is supposed to prevent skin irritations. The vesicular constituents used are hydrated lipids and, for example, cholesterol and sitosterol. However, the vesicles of the resulting liposomes are large in particle size, and are accompanied by numerous expected disadvantages. Therefore, it is more reasonable to strive for smaller size liposomes.

In addition to particle size, the dimensional stability of the liposome preparations and the extent of their permeability are also decisively important for their effective therapeutic or cosmetic use.

The liposome membrane consists of conically-shaped lecithin and in the present case also fatty acid esterified collagen hydrolysate (FAECH) molecules. A bilayer association of these molecules always forms a curved plane, leading finally to the formation of hollow spheres. Since the intermolecular distances are irrefutable given by the physico-chemical nature of these compounds, the diameter of a liposome is directly related to the number of membrane-forming molecules.

An increase in vesicle size always implies an increase of the number of membrane-forming molecules per vesicle (because a liposome cannot swell). Since any liposome preparation is a closed system, such a dimensional increase as mentioned before can occur only by fusion of liposomes. This process results in the formation of a common membrane with twice the number of molecules and a greater diameter than each vesicle had before. Fusion of vesicles always results in a decrease in the number of liposomes in a preparation.

The benefit of liposomes in comparison with conventional topical formulations (such as creams, gels, ointments) is an enhanced penetration of the drug into deeper layers of the skin. The extent of penetration is dependent on size and number of the vesicles, the deepness of penetration on the size of the liposomes. The therapeutic effectiveness of a liposomal preparation increases with the number and the smallness of its vesicles.

During the fusion-process an at least partial release of an encapsulated (water-soluble) active ingredient, e.g., drug, takes place. Finally, fusion to some few large vesicles can also result in sedimentation of the liposomes in the preparation, thus leading to an inhomogeneous distribution of the active substance and, as a consequence, a reduced dose or an overdose of the encapsulated active ingredient.

To summarize, an increase in size is the first and main indicator of physical instability of liposomes. All the subsequent observations as sedimentation, permeability giving rise to a decrease in encapsulated drug, and inhomogeneous distribution and diminished therapeutic effectiveness of the liposomal preparation, are logical and inevitable consequences.

Exactly all these problems are solved by stabilizing lecithin liposomes according to the present invention with certain collagen hydrolysates, thus preventing the previously-inevitable gradual increase of vesicle size during storage.

As already described, liposomes mediate the penetration of a pharmaceutical agent into the skin or systemically. The degree of penetration and the amount of active substance mediated depends on the size of the liposomes. As compared to large liposomes, small liposomes are able to reach deeper skin layers and to transport a greater amount of substance into these layers or into a systemic target. Liposomes of a size smaller than 30 nm are even able to penetrate the skin, thereby entering circulation. In this case, of course, the liposome-mediated active substance does not act in the skin but has a systemic effect. On the contrary, large liposomes having a size of over 60 nm get caught in the upper skin layers where they release the active substance. From the therapeutic point of view, it is very important to be able to provide tailor-made vesicle sizes for specific indications.

For example, when the acid mantle of the skin is pathologically changed and the skin develops a tendency to drying out, scaling, reddening, etc. (neurodermitis), formulations containing relatively large liposomes (>60 nm) should be employed to form an artificial protective lipid film on the skin surface.

In acne formulations, the liposomes should have a size between 35 and 50 nm. These vesicles penetrate deep into the skin and transport the pharmaceutical agent to its deeply located site of action, the pilosebaceous glands.

If a systemic effect is envisaged by using a liposomal formulation (insulin in diabetes mellitus; beta-blockers in the case of asthma/cardiac insufficiency), then the vesicles must penetrate the skin. For this purpose a liposomal size smaller than 30 nm is recommendable.

The production of such tailor-made liposomes by the present approach and method has so far not been described or even suggested. Vesicles of varying size could so far only be produced by means of different manufacturing technologies or by qualitatively changing the formulation (which means substitution or addition of individual ingredients).

In the present process, only one technology is required (high-pressure homogenization or ethanol injection) and the qualitative formulation remains unchanged; only the lecithin/lipoamino acid/lipopeptide proportions need be varied.

In all the aforementioned applications, the selected size of the liposomes must be stable. If there was a growth in particle size, the liposomes designed for systemic treatment would no longer be able to penetrate the skin, or liposomal acne formulations would remain on the skin. In both cases, the formulations would thus become ineffective.

Besides the possibility of, for the first time, producing tailor-made liposomes having a targeted size, especially designed to meet defined therapeutic requirements, the present invention, requiring combination with lecithin of a lipoamino acid or lipopeptide ester in the given concentration range, without more, ensures a stable size of the liposomes over the entire storage period.

From a galenical point of view, the therapeutic application of liposome preparations has often been problematic and limited because of their permeability, dimensional instability, and the particular active ingredient incorporated. One of the main problems is also a degradation of the active ingredient. Route and rate of decomposition are specific and vary from substance to substance. Oxidation processes can be reduced by using suitable antioxidants such as butylhydroxytoluene (BHT) or Vitamin E, whereas pH-dependent hydrolysis can be reduced by suitable buffers. In the case of substances sensitive to such procedure, hydrolysis can still be increased by intensified contact with water, but they can be stabilized by sufficient incorporation in the bilayer. Decisive for the stability of the active ingredient are the decomposition reaction involved and the physico-chemical properties of the substance.

Besides decomposition of the active ingredient, as described above, the liposomes themselves can be affected by lipid oxidation, lipid hydrolysis, and especially aggregation. Lipid oxidation can be reduced through addition of antioxidants as described by A. A. Hunt, S. Tsang, in Int. J. Pharm. 8, 101 (1981) or by A. W. T. Konings in Liposome Technology, Vol. I. Alternatively, there is the possibility of using lecithins with non-oxidizable saturated fatty acid ester groups which cannot be oxidized (cf. P. Kibat, Dissertation, University of Heidelberg, 1987). Hydrolysis of lecithins to lysolecithins can be reduced by buffering the system within a pH range between 6 and 7 (cf. S. Froeckjear et al., Optimization of Drug Delivery, A. Benzon Symposium 17, Kopenhagen (1982)).

Moreover, especially with small unilamellar vesicles (SUV), undesirable particle aggregation can occur already after a few weeks. During this process, the properties of the vesicles change and diminish the shelf-life of a product. The measures attempted so far to combat such changes have comprised the use of hydrated (saturated) lipids or cholesterol up to 50 mol-% in relation to the total lipid content (cf. P. Kibat). Such measures alone have not been successful. The technical processing of hydrated lipids is often more difficult, and they are accordingly less preferred than natural lecithins from eggs, soy beans, and the like.

When using cholesterol for stabilization purposes, the reduced bilayer-binding of lipophilic constituents is often problematic because of a competitive displacement through cholesterol (cf. Mentrup, Dissertation, University of Heidelberg, 1988), resulting in aggregation, particle dimension instability, and undesirable permeability and leakage, just as shown by Handjani (discussed hereinafter). Depending on the characteristics of the active ingredients, the bilayer-binding of therapeutically-effective amounts may be impossible in such a system.

Proceeding directly along such unacceptable lines, just as FR-A 2 591 105, is Handjani et al. published FRG application DE 3713493A1, published on Oct. 29, 1987, which employs a component A (a synthetic lipid) or possibly lecithin and a fatty acid esterified collagen hydrolysate, but also substantial amounts of cholesterol, in the production of vesicles or liposomes which, clearly according to Handjani, cannot contain higher than 15% of a fatty acid-esterified collagen hydrolysate since the impermeability of the vesicles should remain within a "tolerable range" and, "if the percentage is higher than 15%, the permeability of the vesicles is too pronounced leading to their dysfunction". This is moreover clear from the Table of Handjani, wherein vesicles were produced having a percentage of 20% by weight of a fatty acid ester of a collagen hydrolysate plus cholesterol, in which case the permeability rose from 13% at zero days to 24% at the end of fifteen days and from 31% at zero days to 57% at the end of fifteen days. Moreover, even with lesser amounts of the fatty acid esterified collagen hydrolysate and cholesterol, the permeability attained at the end of fifteen days was in almost every case totally unacceptable from the standpoint of storage stability and long-term effectiveness. Copies of the Handjani reference in German and a certified translation thereof into English have been furnished the Examiner during prosecution of the parent application. Handjani teaches that with increasing collagen hydrolysate content of the formulation, the permeability of the membrane reaches a level at which the stability of the dispersion is affected, the resulting fusion of the liposomes leading to increasing particle diameters.

Therefore, Handjani uses the collagen hydrolysate in a range between 1 and maximally 15%. Within this range, the topical properties are slightly improved as compared to the formulation not containing collagen hydrolysate but the liposomes are permeable to the encapsulated substance (see permeability values of 5–57% in the Table on page 7). A vesicle permeability of even 5% is totally unacceptable, especially when it commences at zero days.

Although this patent disclosure is mainly concerned with allegedly novel so-called "non-ionic amphiphilics", more properly designated "amphiphatics", namely, Handjani's synthetic lipid component A having an ether and polyglycerol structure, and although the vesicles or liposomes produced according to that patent disclosure are allegedly between 0.025 and 5 μm, the fact is that the only liposomes or vesicles produced according to the Examples have a size of 0.5 μm, 1 μm, 1.0 μm, 0.5 μm, less than 1 μm, 0.2 μm, 1 μm, 0.3 μm, 1 μm, 0.2 μm, 0.2 μm, and 0.2 μm, which can hardly be considered "small" vesicles since 0.2 μm is equivalent to 200 nm. The only example of this patent which employs lecithin is Example 3, which also employs one-third as much cholesterol as lecithin and only one-eighth as much of a fatty acid ester of a collagen hydrolysate, and produces a vesicle having a mean vesicle size "smaller than 1 μm". In addition to producing only relatively large vesicles, this patent makes no disclosure or suggestion of any way in which vesicle size even might possibly be controlled or particle size reduced, much less by using increased ratios of fatty acid ester of a collagen hydrolysate, and still much less at any percentage greater than 15% of the lipid phase, at which percentage the patent states categorically that its vesicles become dysfunctional due to permeability. Example 3 of the Handjani reference, not unimportantly, shows the employment of the fatty acid-esterified collagen hydrolysate at 8%, the employment of cholesterol at 22%, and the employment of soy lecithin at 66%, said percentages being of the lipid phase and, as previously stated, only one-eighth as much fatty acid-esterified collagen hydrolysate as lecithin or approximately 12.5% thereof, whereas the cholesterol comprised one-third or 33⅓% of the lecithin and almost three times the amount of the fatty acid esterified collagen hydrolysate.

Applicants have found that, when employing lecithin and a fatty acid esterified collagen hydrolysate of a particular type and a mixture consisting essentially thereof, and not cholesterol or a synthetic lipid of Handjani's type A, and providing a vesicle or liposome wall consisting essentially of the lecithin and the fatty acid ester of a collagen hydrolysate (FAECH) of the particular hereinafter-defined type, there is no problem in maintaining the impermeability of the vesicles produced and, moreover, the stability of the particles is at a maximum and aggregation is essentially non-existent so that optimum particle size, stability, non-aggregation, and impermeability are maintained in the vesicles or liposomes provided according to the present invention, quite to the contrary of any teaching of Handjani. Moreover, applicants have found that vesicle dimensional control and particle size reduction can be attained by employing relatively high ratios of the selected FAECH to lecithin, far beyond those which have been stated by Handjani to be inoperative and, in fact, amounts of FAECH to lecithin extending all the way from 10% to 90% of the lipid phase, in the absence of cholesterol or other of Handjani's ingredients which interfere with the desired results of the present applicants, are not only productive of small-size and entirely satisfactory vesicles from every conceivable standpoint but that ratios of the selected FAECH, of a particular type as hereinafter defined, to the lecithin (which are totally contraindicated and in fact stated to be inoperative by Handjani) can be employed to attain a particle size of the vesicles or liposomes produced in inverse proportion or relation to increased ratios of FAECH to lecithin, an important dimensional control which has not been taught, suggested, or even vaguely adumbrated by the prior art, but rather directly contraindicated thereby.

OBJECTS OF THE INVENTION

It is an object of the present invention to provide novel liposome or vesicle compositions consisting essentially of lecithin and between about 10 and 90%, preferably 16 and 90%, and especially between about 20 and 80%, by weight of a fatty acid-esterified collagen hydrolysate (FAECH) selected from fatty acid esterified lipoamino acids and lipopeptides, wherein the fatty acid contains from 8 to 24 carbon atoms, and a method for the preparation thereof, as well as the important aspect of vesicle dimensional control and particle size reduction by employing increased ratios of the specified fatty acid-esterified collagen hydrolysate, and further a method for the use thereof in cosmetic and/or pharmaceutical preparations or compositions, and the compositions themselves containing effective amounts of cosmetically or pharmaceutically-effective active ingredients, the vesicles or liposomes according to the present invention being characterized by unprecedented stability, non-aggregating properties, and impermeability, and wherein the particle size of the vesicle or liposome is reduced in proportion to an increase in the weight ratio of the specified fatty acid-esterified collagen hydrolysate to the lecithin present in the vesicle wall and in the mixture of ingredients employed in the production of the same. Other objects of the invention will be apparent to one skilled in the art and still other objects of the invention will become apparent as the description of the present invention proceeds.

SUMMARY OF THE INVENTION

What we believe and claim to be our invention, therefore, inter alia comprises the following, alone or in combination:

A liposome preparation wherein the vesicles are impermeable, non-aggregating, and have a dimensionally-stable small particle size of about 20 to 150 nm and a vesicle membrane which consists essentially of a mixture of 90 to 10% by weight of lecithin or another synthetic or natural phosphatidyl choline having a saturated or unsaturated C16–C20 fatty acid chain, and 10 to 90% by weight of a fatty acid-esterified lipoaminoacid or fatty acid-esterified lipopeptide wherein the esterifying fatty acid is a C8–C24 carboxylic acid; such a a liposome preparation, wherein the vesicle membrane contains 16–90% by weight of fatty acid-esterified lipoaminoacid or lipopeptide; such a liposome preparation, wherein the vesicle membrane contains 20–80% by weight of fatty acid-esterified lipoaminoacid or lipopeptide; such a liposome preparation, wherein the fatty acid-esterified lipoaminoacid or lipopeptide is selected from the group consisting of collagen oleoyltetra- and pentapeptide, caproyl collagen aminoacids, myristoyl hydrolyzed animal protein, dipalmitoyl hydroxy proline, and palmitoyl collagen aminoacids; such a liposome preparation, wherein the fatty acid-esterified lipoaminoacid or lipopeptide is collagen oleoyl tetra- and pentapeptide; such a liposome preparation, wherein the lecithin is a natural lecithin and the particle size of the vesicles is 20 to 70 nm; such a liposome preparation, wherein the lecithin is soy or egg lecithin and the particle size of the vesicles is 20 to 70 nm; such a liposome preparation, wherein the fatty acid-esterified lipoaminoacid or lipopeptide is selected from the group consisting of collagen oleoyltetra- and pentapeptide, capryloyl collagen aminoacids, myristoyl hydrolyzed animal protein, dipalmitoyl hydroxy proline, and palmitoyl collagen aminoacids; such a liposome preparation, wherein the fatty acid-esterified lipoaminoacid or lipopeptide is collagen oleoyl tetra- and pentapeptide; such a liposome preparation, wherein the liposomes are dispersed in a gel; such a liposome preparation, wherein the gel is selected from gels incorporating a polyacrylic acid, a gel-forming cellulose compound, or a sodium salt of an acrylic acid-acrylamide copolymerisate; such a liposome preparation, wherein the liposomes additionally contain a therapeutic or cosmetic agent; such a liposome preparation, wherein the agent is selected from hexachlorophene, tretinoin, minocycline, meclocycline, sodium heparin, α-tocopherol nicotinate, tromantadine base, croconazole, dexpanthenol, cyproterone, cyproterone acetate, 2-tert.-butyl-4-cyclohexylphenyl nicotinate-N-oxide, ethinyl estradiol, and spironolactone; such a liposome preparation, wherein the agent is selected from corticosteroids, androgens, non-steroidal antiphlogistics, dihydropyridines, erythromycin esters, plant extracts, local anesthetics, estradiol esters, and antihistaminics; such a liposome preparation, wherein the vesicles are multilamellar; and such a liposome preparation, wherein the vesicles are unilamellar.

Moreover, a cosmetic composition suitable for topical application to humans comprising such a liposome preparation, wherein the liposomes contain an effective amount of a cosmetically- and topically-effective active ingredient, and a cosmetically-acceptable carrier or diluent, and a pharmaceutical composition suitable for topical application to humans comprising such a liposome preparation, wherein the liposomes contain an effective amount of a pharmaceutically- and topically-effective active ingredient, and a pharmaceutically-acceptable carrier or diluent; such a cosmetic composition, wherein the active ingredient is lipid soluble and is present in the vesicle wall or membrane; such a cosmetic composition, wherein the active ingredient is water soluble and is encapsulated within the vesicle walls; such a pharmaceutical composition, wherein the active ingredient is lipid soluble and is present in the vesicle wall or membrane; and such a pharmaceutical composition, wherein the active ingredient is water soluble and is encapsulated within the vesicle walls.

Additionally, a process for the manufacture of a liposome preparation wherein the vesicles are impermeable, non-aggregating, and have a dimensionally-stable small particle size of about 20 to 150 nm and a vesicle membrane which consists essentially of a mixture of 90 to 10% by weight of lecithin or another synthetic or natural phosphatidyl choline having a saturated or unsaturated C16–C20 fatty acid chain, and 10 to 90% by weight of a fatty acid-esterified lipoaminoacid or fatty acid-esterified lipopeptide wherein the esterifying fatty acid is a C8–C24 carboxylic acid, wherein (a) the lecithin or other phosphatidyl choline is dispersed with 10 to 90% by weight of fatty acid-esterified lipoaminoacid or lipopeptide; and (b) the dispersion produced according to step (a) is mixed with a jellifying agent; such a process, wherein the dispersion obtained according to step (a) is further reduced in particle size and homogenized; such a process, wherein in step (a) a mixture of lecithin, fatty acid-esterified lipoaminoacid or lipopeptide, and ethanol is injected into an aqueous phase; such a process, wherein the vesicles are multilamellar; such a process, wherein the lecithin is a natural lecithin, the amount of fatty acid-esterified lipoaminoacid or lipopeptide is 20–80% by weight, and the vesicle particle size is reduced to 20–70 nm; such a process, wherein the fatty acid-esterified lipoaminoacid or lipopeptide is collagen oleoyl tetra- and pentapeptide; such a process, wherein the vesicles are unilamellar; and such a method, wherein an active therapeutic or cosmetic ingredient is additionally included in the dispersion; such a method, wherein an active ingredient selected from hexachlorophene, tretinoin, minocycline, meclocycline, α-tocopherol nicotinate, tromantadine base, croconazole, sodium heparin, cyproterone, cyproterone acetate, 2-tert.-butyl-4-cyclohexylphenyl nicotinate-N-oxide, ethinyl estradiol, dexpanthenol, and spironolactone is included in the dispersion; such a method, wherein an active ingredient selected from corticosteroids, androgens, non-steroidal antiphlogistics, plant extracts, dihydropyridines, erythromycin esters, local anesthetics, estradiol esters, and antihistaminics is included in the dispersion; such a process, wherein in step (b) polyacrylic acid, a gel-forming cellulose compound, or a sodium salt of an acrylic acid-acrylamide copolymerisate is employed as jellifying agent; such a process, wherein the concentration of the lecithin and fatty acid-esterified lipoaminoacid or lipopeptide in the resulting dispersion from step (a) is between about 5 and 350 mg/ml; such a process, wherein the concentration of the lecithin and fatty acid-esterified lipoaminoacid or lipopeptide in the resulting dispersion from step (a) is between about 20 and 180 mg/ml; such a process, wherein the percentage of lecithin and fatty acid-esterified lipoaminoacid or lipopeptide in the resulting dispersion from step (a) is between about 0.5 and 35 percent by weight; and such a method, wherein the mixture and the resulting vesicle membrane contain 16–90% by weight of fatty acid-esterified lipoaminoacid or lipopeptide; such a method, wherein the mixture and the resulting vesicle membrane contain 20–80% by weight of fatty acid-esterified lipoaminoacid or lipopeptide; such a method, wherein the fatty acid-esterified lipoaminoacid or lipopeptide is selected from the Group consisting of collagen oleoyltetra- and pentapeptide, capryloyl collagen aminoacids, myristoyl hydrolyzed animal protein, dipalmitoyl hydroxy proline, and palmitoyl collagen aminoacids; such a method, wherein the fatty acid-esterified lipoaminoacid or lipopeptide is collagen oleoyl tetra- and pentapeptide; such a method, wherein the lecithin is a natural lecithin and the particle size of the vesicles is reduced to 20 to 70 nm; such a method, wherein the lecithin is soy or egg lecithin and the particle size of the vesicles is reduced to 20 to 70 nm; such a method, wherein the fatty acid-esterified lipoaminoacid or lipopeptide is selected from the group consisting of collagen oleoyltetra- and pentapeptide, capryloyl collagen aminoacids, myristoyl hydrolyzed animal protein, dipalmitoyl hydroxy proline, and palmitoyl collagen aminoacids; such a method, wherein the fatty acid-esterified lipoaminoacid or lipopeptide is collagen oleoyl tetra- and pentapeptide; such a process, wherein the size of the vesicles produced is regulated by controlling the percentage of fatty acid-esterified lipoaminoacid or lipopeptide employed in the dispersion within the prescribed range to produce liposomes, the dimensions of which are reduced corresponding to an increase in the percentage of fatty acid-esterified lipoaminoacid or lipopeptide employed, and including the step of controlling the said percentage to produce vesicles of desired dimensions; such a method, wherein the liposomes containing an effective amount of a cosmetically- and topically-effective active ingredient are combined with a cosmetically-acceptable carrier or diluent; and such a method, wherein the liposomes containing an effective amount of a pharmaceutically- and topically-effective active ingredient are combined with a pharmaceutically-acceptable carrier or diluent.

Finally, a method of controlling and determining the size between about 20 and 150 nm of small-sized essentially impermeable liposomes, which are dimensionally stable and non-aggregating, the vehicle membrane of which consists essentially of between 90 and 10% by weight of lecithin or another synthetic or natural phosphatidyl choline having a saturated or unsaturated C16–C20 fatty acid chain and 10 to 90% by weight of a fatty acid-esterified lipoaminoacid or lipopeptide wherein the esterifying fatty acid is a C8–C24 carboxylic acid, which consists essentially in controlling the percentage of fatty acid-esterified lipoaminoacid or lipopeptide in the membrane within the prescribed range to produce liposomes, the dimensions of which are reduced corresponding to an increase in the percentage of fatty acid-esterified lipoaminoacid or lipopeptide employed, and including the step of controlling the said percentage to produce liposomes of desired dimensions; such a method, wherein the percentage by weight of fatty acid-esterified lipoaminoacid or lipopeptide employed is between about 16 and 90% by weight; such a method, wherein the percentage by weight of fatty acid-esterified lipoaminoacid or lipopeptide employed is between about 20 and 80% by weight, and wherein a natural lecithin is employed; such a method, wherein the fatty acid-esterified lipoaminoacid or lipopeptide is selected from the group consisting of collagen oleoyltetra- and pentapeptide, capryloyl collagen aminoacids, myristoyl hydrolyzed animal protein, dipalmitoyl hydroxy proline, and palmitoyl collagen aminoacids; and such a method, wherein the fatty acid-esterified lipoaminoacid or lipopeptide employed is collagen oleoyl tetra- and pentapeptide.

GENERAL DESCRIPTION OF THE INVENTION

Lecithin

The term lecithin has been defined in an official monograph of the USP for years. A copy of the cover sheet of The United States Pharmacopeia, the National Formulary, USP XXII and NFXVII, published in 1989 and official from Jan. 1, 1990, has been provided to the Examiner in the parent application. On pages 1942 and 1943 thereof, the official monograph of lecithin is clearly set forth.

The best-suited building elements for liposome preparations are soy or egg lecithin. In addition to these two natural lecithins, other synthetic or natural phosphatidyl cholines with saturated or unsaturated fatty acid chains of 16–20 carbon atoms can also be used. In addition to soy and egg lecithins, also rape and safflower lecithins are of natural origin. The definition of fatty acid chain lengths of 16–20 carbon atoms representatively comprises palmitic acid, margaric acid, stearic acid, nonadecanoic acid, arachic acid, palmitoleic acid, oleic acid, linoleic acid, linolenic acid, elaeomargaric acid, elaeostearic acid, gadoleic acid, and arachidonic acid. As will be understood by one skilled in the art, since phosphatidylcholine (PC) should be esterified twice, the resulting PC esters, which are in fact the phosphatidylcholines, are for example: dioleoyl-PC, dipalmitoyl-PC, but also mixed esters such as margaroyl-stearoyl-PC, palmitoyl-oleoyl-PC, and the like. These well-defined phosphatidylcholines are not produced by extraction or otherwise from natural lecithins, but are synthesized de novo and are consequently referred to as synthetic lecithins.

Fatty acid-esterified collagen hydrolysates (FAECH)

Fatty acid-esterified collagen hydrolysates can be classified according to the number of amino acids combined with a fatty acid according to the following:

lipoaminoacid (1 aminoacid=fatty acid-single aminoacid conjugate)

lipopeptide (2–10 aminoacids=acyl oligopeptide).

According to the present invention, lipoproteins, that is, having greater than 10 amino acids and therefore being acyloxy polypeptides, are not of interest.

Accordingly, instead of the term fatty acid-esterified collagen hydrolysates, the terms lipoaminoacid, of which 4-hydroxyproline is the most preferred amino acid, and/or lipopeptide, wherein the number of amino acids is limited to $n_{max}=10$, preferably n=2–5, may be employed and, in any case, wherein in these compounds the esterified fatty acid is selected from $C_8$–$C_{24}$ saturated and mono- and polyunsaturated fatty acids, of which caprylic acid, lauric acid, myristic acid, undecylenic acid, palmitic acid, stearic acid, and oleic acid are preferred.

According to the present invention, between about 10 and 90% of the FAECH, preferably 16–90% of the FAECH, and most preferably 20 to 80% of the fatty acid-esterified collagen hydrolysate is incorporated along with the lecithin into the vesicle walls or membranes. Especially preferred are the oleic acid-esterified collagen hydrolysates (OHAP or oleyl hydrolyzed animal protein) and others which are set forth hereinafter. These materials are amphiphatic tensides. Although they have been used as stabilizers in pharmaceutical and cosmetic creams, they have so far not been used or suggested to stabilize liposomes. Such fatty-acid esterified collagen hydrolysates (FAECH) are prepared by the condensation of hydrolysis products of animal protein with the chloride of the selected $C_8$–$C_{24}$ fatty acid, which may also be besides oleic acid, for example, palmitic, stearic, linoleic, ricinoleic, coconut, abietic, or linolenic acid.

Further Description of the Invention

Fatty acid esters of lipopeptides and lipoamino acids are generally produced by combining the peptide, amino acid, or collagen hydrolysate with a fatty acid. This combination results from a linkage between the carboxyl group of the fatty acid chain and the amine group of the peptide, amino acid, or collagen hydrolysate. Fatty acid chlorides generally react with the peptide/amino acid/collagen hydrolysate, the resulting product being precipitated using an acid. For purification, the reaction product is again washed with solvent which is subsequently distilled off. Many such materials are commercially available, for example, Lamepon™ LPO, Lipacide™ PCO, Lipacide™ DPHP, Lexein™ A 200, and Lipacide™ C8CO, these being further identified as follows:

PCO - Palmitoyl Collagen Amino Acids - (Lipacide™PCO; palmitic acid-single aminoacid conjugate, wherein 4 -hydroxy-proline is the main amino acid, and therefore a lipoaminoacid) (formerly Rhone-Poulenc, now Seppic, Paris, France).

DPHP - Dipalmitoylhydroxyproline (Lipacide™DPHP; O-N-dipalmitoyl derivative of 4-hydroxyproline, and therefore a lipoaminoacid) (Seppic).

MHAP - Myristoyl Hydrolyzed Animal Protein (Lexein™ A200; myristoyltripeptide, and therefore a lipopeptide), marketed by INOLEX Chemical Co., Chicago, Ill.

C8CO - Caryloyl Collagen Amino Acids (Lipacide™ C8CO; caprylic acid-single aminoacid conjugate, wherein 4-hydroxyproline is the main amino acid, and therefore a lipoaminoacid) (Seppic).

OHAP=Collagen oleoyltetra- and pentapeptide, marketed by Henkel KGaA, Düsseldorf, Germany under the name "Lamepon™ LPO". (OHAP is an abbreviation for "oleoyl hydrolyzed animal protein").

The total concentration of lecithin and one or more of the specified fatty-acid esterified collagen hydrolysates (FAECH), i.e., lipoamino acid or lipopeptide ester, in the resultant aqueous dispersion is generally between 5 and 350 mg/ml, preferably between 20 and 180 mg/ml. This corresponds to about 0.5 to 35% or preferably 2–18% lecithin and fatty-acid esterified collagen hydrolysate by weight in the liposome preparation. The addition to lecithin of fatty-acid esterified collagen hydrolysate, representatively OHAP, produces liposomes much smaller in size than would be obtained without this additive, which affords the above-described advantages. Such advantageous effect has previously not been obtained with liposomes containing active ingredients. Only with substance-free liposomes has a reduction in vesicular size been achieved previously by addition of a few other substances with amphiphatic character. The following Table 1 shows the influence of various substances commonly used in liposome technology on the particle size of the liposomes produced in a high-pressure homogenizer, i.e., according to the same process. When producing large liposomes from soy lecithin by the handshake method (cf. A.D. Bangham et al., J. Mol. Biol. 13, 238 (1965)), the liposomes containing an added amphiphatic substance (e.g., cholesterol) are much larger than the original vesicles. The employment of fatty-acid esterified collagen hydrolysate, representatively OHAP, with lecithin according to the present invention and without the employment of cholesterol or Handjani's Component A, however, does effect a marked stabilization and even a reduction in particle size, as described in the following. Therefore, the influence on vesicle size is essentially independent of the process employed, but is rather substance-determined, that is, by the weight ratio or percentage of the FAECH employed to the lecithin employed.

TABLE 1

Influence of various substances on the size of substance-free lipid vesicles
(Process: High-pressure homogenizer, 30 min. $1.4 \cdot 10^8$ Pa)

| Concentration soy lecithin (mg/ml) | Lipid component | Concentration lipid component (mg/ml) | Vesicle size (nm) |
|---|---|---|---|
| 100 | — | — | 40 ± 10 |
| 80 | OHAP | 20 | 25 ± 4* |
| 80 | medium-chain triglycerides | 20 | 71 ± 15 |
| 80 | Squalene | 20 | 57 ± 12 |
| 80 | Cholesterol | 20 | 58 ± 14** |
| 80 | Polyoxyethylene-oleyl ether | 20 | 34 ± 7 |
| 80 | Polysorbate 80 | 20 | 24 ± 4† |
| 96 | Polysorbate 80 | 4 | 25 ± 5 |

*= down
**= up
†= down BUT unacceptable

Polysorbate 80 is the only tenside which, in substance-free liposomes, effects a marked reduction in vesicle size (cf. B. Kronberg et al., J. Pharm. Sci., 70 (8), 667–71 (1990)). However, in liposomes containing substances such as tocopherol nicotinate or hexachlorophene, the addition of polysorbate 80 (e.g. 20%) leads to a marked increase in particle size with inhomogeneous distribution. Therefore, this substance is not suited for the manufacture of pharmaceutically-stable products.

As already mentioned, the use of a specified fatty acid-esterified collagen hydrolysate according to the invention effects a reduction of vesicle size also in the presence of lipophilic therapeutics. Lipophilic agents suitable for bilayer-binding are, for example, acne therapeutics such as hexachlorophene, tretinoin, or minocycline. Other topical agents such as α-tocopherol nicotinate, tromantadine base, croconazole, minocycline, sodium heparin, dexpanthenol, meclocycline, cyproterone, cyproterone acetate, corticoids, 2-tert.-butyl-4-cyclohexylphenyl nicotinate-N-oxide, plant extracts, corticosteroids, androgens, ethinyl estradiol, non-steroid antiphlogistics, dihydropyridines, spironolactone, erythromycin esters, local anaesthetics, estradiol esters, or antihistaminics can also be incorporated. The amount of active substance can be varied in dependence upon the therapeutic requirements. For example, 10 mg to 50 g of active ingredient can be used per 100 g of lecithin-fatty acid-esterified collagen hydrolysate (e.g., OHAP) admixture. This affords the possibility of incorporating such agents into liposomes with very small vesicle size. Based on the general vesicle size, an increase in therapeutic activity is possible due to the small diameter and stability thereof attainable according to the present invention.

A special advantage of incorporating fatty acid-esterified collagen hydrolysate (FAECH) in lecithin liposomes according to the present invention, consisting essentially only of the lecithin and the FAECH, is that, by the addition of varying amounts thereof, which are incorporated into the vesicle membrane, the desired vesicle size can be controlled within a broad range as is shown in the following Table 2 wherein the FAECH content is 0, 20, 50, and 80%, and the vesicle size is reduced inversely with an increase in the FAECH ratio employed.

TABLE 2

Influence of OHAP percentage on the vesicle size
of tocopherol nicotinate-containing liposomes
(Process: High-pressure homogenization - 30 min. $1.4 \cdot 10^8$ Pa)

| Concentration soy lecithin (mg/ml) | Concentration OHAP (mg/ml) | and %/wt. | Vesicle size (nm) |
|---|---|---|---|
| 100 | — | 0 | 51 ± 14 |
| 80 | 20 | 20 | 42 ± 17 |
| 50 | 50 | 50 | 25 ± 5 |
| 20 | 80 | 80 | 26 ± 5 |

The following Table 3 shows that by the addition of OHAP the particle size of larger liposomes obtained by ethanol injection can also be controlled.

TABLE 3

Influence of OHAP Percentage on the vesicle size
of substance-free liposomes
(Process: Ethanol injection according to Example 6)

| Concentration soy lecithin (mg/ml) | Concentration OHAP (mg/ml) | and %/wt. | Vesicle size (nm) |
|---|---|---|---|
| 32 | — | 0 | 637 ± 309 |
| 32 | 8 | 20 | 175 ± 106 |
| 24 | 12 | 33⅓ | 109 ± 26 |
| 24 | 24 | 50 | 99 ± 26 |

As can be seen from Tables 2 and 3, the extent to which vesicle size reduction can be effected in substance-loaded liposomes depends on the increased ratio of OHAP or other FAECH employed (i.e., 0, 20, 33⅓, and 50% by weight), but is also somewhat dependent upon the active ingredient. This is particularly apparent from Table 2.

An essential factor for the large-scale application of liposomes is the liposomes' storage stability as already described. The most important physical parameter of the storage stability is the size of the vesicles. Vesicle aggregation, which especially occurs using lecithin alone, can be markedly reduced or eliminated by the incorporation of a suitable fatty acid-esterified collagen hydrolysate (for example, according to Example 2) as shown in Table 4. These liposomes according to the present invention, consisting essentially only of the lecithin and the selected fatty acid esterified collagen hydrolysate (FAECH), are therefore smaller and stable under storage conditions. A loss in therapeutic effect occurring as a result of aggregation is thus prevented. In addition, possible chemical liposome instability can be reduced by reduction of the lecithin portion (due to inclusion of OHAP or other selected FAECH). It is only the lecithin that can be affected by the destabilizing formation of lysolecithin. Thus, the associated toxic effect can be considerably reduced by employing greater proportions of one or more of the selected FAECHs according to the invention.

The following Table 4 shows a comparison of the stability of the preparations according to the invention.

TABLE 4

Stability of OHAP-containing tocopherol nicotinate liposome

| Lipid | Total lipid concentration (mg/ml) | Vesicle size (nm) after | | | |
|---|---|---|---|---|---|
| | | 0 | 4 | 12 | 24 |
| | | | (weeks) | | |
| Soy Lecithin (comparison) | 100 | 90 ± 19 | 96 ± 23 | 196 ± 188 | 274 ± 191 |
| Soy Lecithin/OHAP 8:2 according to Example 2 (invention) | 100 | 49 ± 14 | 45 ± 14 | 44 ± 10 | 42 ± 11 |

The Table shows that the storage stability of the liposomes consisting essentially of the lecithin and an FAECH according to the invention is much better than that of comparable liposomes not containing OHAP, the particle size actually diminishing upon storage compared to a 3× size increase for the lecithin-only vesicles.

Stability of Lecithin-OHAP tocopherol nicotinate liposomes
(Supplement to Table 4)

| soy lecithin/ OHAP-ratio | total lipid concentration [mg/ml] | vesicle size [mm] after [weeks] | | | |
|---|---|---|---|---|---|
| | | 0 | 4 | 12 | 24 |
| 100:0 | 100 | 90 ± 19 | 96 ± 23 | 196 ± 188 | 274 ± 191 |
| 95:5 | 100 | 93 ± 20 | 100 ± 20 | | 102 ± 22 |

Stability of Lecithin-OHAP tocopherol nicotinate liposomes
(Supplement to Table 4)

| soy lecithin/ OHAP-ratio | total lipid concentration [mg/ml] | vesicle size [mm] after [weeks] | | | |
|---|---|---|---|---|---|
| | | 0 | 4 | 12 | 24 |
| 90:10 | 100 | 60 ± 18 | 62 ± 14 | 60 ± 14 | 63 ± 15 |
| 80:20 | 100 | 49 ± 14 | 45 ± 14 | 44 ± 10 | 42 ± 11 |
| 70:30 | 100 | 41 ± 11 | | 38 ± 11 | 38 ± 11 |
| 50:50 | 100 | 39 ± 10 | 40 ± 9 | 37 ± 9 | 38 ± 9 |

There is clear evidence from this data, that already 5% of OHAP distinctly improves the liposome stability. Except for the resulting desirable vesicle size, which in the present case should be as small as possible, the totally stabilizing effect of OHAP occurs already at a concentration of 10%!

The stabilization of liposomes by polysorbate described by B. Kronberg et al. can be demonstrated over only a short storage period. As already described, particularly substance-containing liposomes are markedly larger and more inhomogeneous than liposomes made of soy lecithin and fatty acid-esterified collagen hydrolysate or OHAP. After a 4-week storage period, the liposomes develop considerable sedimentation which is not acceptable for a pharmaceutical product. Therefore, polysorbate as an additive to substance-containing liposomes is not suited for vesicle size reduction and stability.

Liposome preparations for topical application are usually mixed with polymer jellifying agents to increase viscosity and improve application. For this purpose, especially polyacrylic acid (0.2 to 1.5%), gel-forming cellulose derivatives (0.2 to 3%) and sodium salts of acrylic acid/acrylamide copolymerisates (CTFA nomenclature − 1 to 4%); commercially available as Hostacerin PN73® in the concentrations indicated are used. When adding such jellifying agents to liposome preparations made of pure lecithin, the vesicles frequently aggregate as a result of interactions with the polymer or otherwise. In contrast to that, the fatty acid-esterified collagen hydrolysate-containing vesicles according to the invention surprisingly show only a slight change in vesicle size after having been made into polymer gels. This is documented in the following Table 5.

significant difference (no increase, but even a decrease in diameter!) However, the "±×nm" data are not standard deviations and the vesicle size-data are not mean but main values. Of course not every liposome has a diameter of 108 nm. Rather the vesicle size varies between 108 nm−23 nm=85 nm and 108 nm+23 nm= 131 nm. But in between these highest and lowest limits (= range of 46 nm) more than 95% of all liposomes are exactly 108 nm in diameter (as further shown in Table 4.) So the main percentage of the liposomes really increased in size from 108 nm to 142 nm after 32 months of storage. Also, the range between highest and lowest limit increased. This likewise shows that the lecithin only liposomes are not stable and tend to fuse. An increase in the range of vesicle size distribution (here: 46 nm to 62 nm) always indicates the formation of some big liposomes beneath the original small ones. The resulting consequences are disadvantageous, as previously described.

In contrast to pure lecithin liposomes, neither the main value nor the range of particle size distribution changes in the case of OHAP-containing liposomes.

Such liposomes according to the invention can be prepared by dispersing a mixture consisting essentially of lecithin, preferably egg or soy lecithin, 10–90%, preferably 16–90%, and especially 20–80%, of a stated fatty-acid esterified collagen hydrolysate (FAECH), in this case OHAP, and, as required, a pharmaceutical agent or other active ingredient as described above and the traditional auxiliary agents in an aqueous phase having an appropriate pH value; preferably about 5–7. The resulting dispersion can be reduced in particle size and homogenized, preferably by high-pressure homogenization.

TABLE 5

Change of vesicle size after incorporation of liposomes into Hostacerin ® gels and subsequent storage at 21° C.

| Lipid | Total lipid concentration (mg/ml) | Vesicle size before jellification (nm) | Vesicle size after jellification (nm) | Vesicle size after storage of | | | | Content of active substance after 32 weeks |
|---|---|---|---|---|---|---|---|---|
| | | | | 5 | 12 | 24 | 32 | |
| | | | | (weeks) | | | | |
| SL | 100 | 95 ± 19 | 108 ± 23 | 110 ± 24 | 117 ± 23 | 124 ± 23 | 142 ± 31 | 92.9% |
| SL/OHAP | 100 | 40 ± 10 | 40 ± 10 | 42 ± 10 | 45 ± 10 | 42 ± 111 | 41 ± 9 | 100% |

SL = soy lecithin

One is correct in seeing no significant changes in size of pure lecithin vesicles only if one considers the "±×nm"-data in Table 5 as standard deviations. In this case there would be an overlapping of the highest starting value (vesicle size after jellification: 108 nm+23 nm= 131 nm) and the lowest final value (142 nm−31 nm=111 nm) and therefore no In addition, the above mixture of lecithin, collagen hydrolysate and auxiliary agents (but excluding cholesterol and Handjani Component A) and, if required, pharmaceutical or cosmetic agent, is preferably injected as an ethanolic solution into an aqueous phase (ethanol injection).

Subsequently, the dispersion can be mixed with the common amounts of a suitable jellifying agent, preferably one of those described above. The gel is prepared according to commonly known procedure.

Especially preferred in the production of the preparations according to the invention are mixtures consisting essentially of egg or soy lecithins with a specified type of fatty-acid esterified collagen hydrolysate, representatively OHAP, the described jellifying agents and active substances, which are homogenized by high-pressure homogenization procedure or by ethanol injection.

Alternatively and optionally, common adjuvants such as, for example, an antioxidant, e.g., vitamin E or butylhydroxy toluene (BHT), and preservatives such as phenoxethol, sorbic acid, Kathon CG™ (Merck Index 11, No. 6677), or parabens can be added in usual amounts.

Moreover, a salient and most important aspect of the present invention is the important aspect of vesicle dimensional control and particle size reduction which, according to the present invention, employing a mixture consisting essentially of lecithin and one or more of the selected and defined fatty acid esterified collagen hydrolysates, is effected by employing controlled ratios of the FAECH to the lecithin, it being clear from the Examples and Tables that the greater the ratio of the FAECH to the lecithin, the smaller the particle size of the vesicle or liposome produced, thus making it possible to employ the step of controlling the said ratio to produce vesicles of desired dimensions. Such a phenomenon is previously unheard of and totally unsuggested by the prior art. Thus, by increasing the FAECH content of the vesicle membrane, in proportion to the lecithin, the vesicle dimension is subjected to control and particle size reduction conveniently effected and attained, the evidence showing that an increase in the percentage of FAECH to the total weight of FAECH and lecithin from 16% up to as high as 80% is most convenient in effecting particle size reduction of the liposomes or vesicles thus produced from, for example 42 nm to 26 nm or 175 nm to 99 nm, depending upon the precise FAECH employed and the type of substance encapsulated by the vesicle or liposome.

The vesicle size of the resultant substance-containing liposome preparations according to the present invention is about 20 to 150 nm, preferably 20 to 70 nm. Depending on the active ingredient used, they are especially suited for topical application as dermatologicals or cosmetics. As compared to traditional products, an increase in therapeutic activity has been observed which is due to an intensified interaction of the vesicles with the skin cells because of their reduced diameter. Additionally, because of the product's higher stability, long-term efficacy without toxic side effects is ensured.

Furthermore, the preparations according to the invention are easy to produce. During this process the described advantages may be utilized without the necessity of employing Handjani's Component A or cholesterol, which, as previously pointed out, are actually disadvantageous from the standpoint of attaining maximum or optimal properties, or even acceptable properties, in the final vesicle product.

DETAILED DESCRIPTION OF THE INVENTION

The invention is further illustrated by the following examples, which are not to be construed as limiting.

Example 1

Preparation of a 20% OHAP-containing liposome gel by high-pressure homogenization Introduce 80 g of soy lecithin, 9 g of phenoxyethanol and 45 g of ethanol into a suitable vessel and heat to 50° C. under stirring. To this clear homogenous liquid add 400 mg of butylhydroxy toluene, 20 g of OHAP and 745.6 g of hypotonic buffer (pH 6.5). Treat the lipid dispersion (900 g) in a high-pressure homogenizer ($1.1,108$ Pa; 40 min.) and subsequently filter through a membrane (0.45 μm).

The gel is prepared by dispersing 5 g of polyacrylic acid (e.g., Carbopol® 984), 1 g of phenoxyethanol and 9.8 g of TRIS buffer in a mixture of 5 g of ethanol and 80.2 g of phosphate buffer (pH 6.5). The gel concentrate is allowed to swell for one day, and then admixed into the liposome dispersion described above.

Example 2

Preparation of a 20% OHAP-containing tocopherol nicotinate liposome gel by high-pressure homogenization Introduce 80 g of soy lecithin, 20 g of α-tocopherol nicotinate, 7.5 g of phenoxyethanol and 37.5 g of ethanol into a suitable vessel and heat to 50° C. under stirring. To the clear homogeneous liquid add 400 mg of butylhydroxy toluene, 20 g of OHAP and 829.5 g of hypotonic phosphate buffer (pH 6.5). The resultant lipid dispersion (990 g) is treated in a high-pressure homogenizer ($1.1.10^8$ Pa; 40 min) and subsequently filtered through a membrane (0.45 μm).

The gel is produced by sprinkling 10 g of carboxymethylcellulose onto 990 g of liposome dispersion and allowed to swell for 24 hours. The liposomes are much more stable under storage conditions than comparable liposomes not containing OHAP. After 1-year storage at 21° C., the active content is 96.9%. Within this period the vesicle size changed only from 27.3±3.8 to 29.5±6.5 nm.

Example 3

Preparation of a 20% OHAP-containing cyproterone liposome gel by high-pressure homogenization Introduce 80 g of soy lecithin, 100 mg of cyproterone, 10 g of phenoxy ethanol and 50 g of ethanol into a suitable vessel and heat to 50° C. under stirring. To the clear homogeneous liquid add 400 mg of butylhydroxy toluene, 20 g of OHAP and 829.5 g of hypotonic phosphate buffer. Treat the resulting lipid dispersion (990 g) by high-pressure homogenization ($1.1.10^8$ Pa; 40 min.) and subsequently filter through a membrane (0.45 μm). The gel is prepared by spreading 10 g of carboxymethyl cellulose or other gel-forming cellulose compound, of which type many are known, onto 990 g of liposomal dispersion under stirring, and allowed to swell for 24 hours. The storage stability of the resulting liposomes is much better than that of comparable liposomes not containing OHAP. After 1-year storage at 21° C., the active content is 96.9%. Within this period the particle size changes only from 27.3±3.8 to 29.5±6.5 nm.

Example 4

Preparation of a 20% OHAP-containing tretinoin liposome gel by high-pressure homogenization Introduce 200 mg of tretinoin and 400 mg of butylhydroxy toluene into a suitable vessel and dissolve in 50 g ethanol under stirring. Disperse 80 g of lecithin, 20 g of OHAP and 10 g of phenoxy ethanol in isotonic phosphate buffer (pH 6.5; 802 g). Pour the ethanolic solution into the aqueous phase under Ultraturrax™ treatment. Treat the resulting dispersion (962.5 g) with a high-pressure homogenizer ($1.1 \cdot 10^8$ Pa; 40 min) and subsequently filter through a membrane (0.45 μm). The liposomes have a vesicle size of 23±4 nm.

The gel is prepared by dispersing 12.5 g of polyacrylic acid (Carbomer 941®) and 25 g TRIS in the liposome dispersion under stirring, and allowed to swell for 24 hours.

The residual tretinoin content after 1 year (storage at 4° C.) was 95.2%, the vesicle size being 29.2±6.4 nm.

Example 5

Preparation of a 20% OHAP-containing croconazole liposome gel by high-pressure homogenization Introduce 1 g of croconazole into a suitable vessel and dissolve in 10 g of ethanol. Under Ultraturrax™ treatment, pour the ethanolic solution into the aqueous phase which contains the lecithin, OHAP and phenoxethol in the proportions of Example 2. Treat the resulting dispersion by high-pressure homogenization ($1.1 \cdot 10^8$ Pa; 40 min) and subsequently filter through a membrane (0.45 μm). The gel is prepared by dispersing 12.5 g of polyacrylic acid (Carbomer 941®) and 25 g TRIS in the liposome dispersion under stirring, and allowed to swell for 24 hours. The pH value of the gel is between 7 and 8. The vesicle size of the liposomes is 22±3 nm.

Example 6

Preparation of a 50% OHAP-containing liposome dispersion by ethanol injection (Also 20% and 33⅓%; See Table 3)

Dissolve 2.4 g of soy lecithin and 2.4 g of OHAP in 20 ml of ethanol and inject into 80 ml isotonic buffer (pH 6.5) by means of a suitable syringe. Inject the solution in an ultrasonic bath to achieve a better dispersion of the ethanolic solution. Then filter the solution through a membrane (0.45 μm). The final concentration is 4.8% lipid and 20% ethanol. The resultant vesicle size is much smaller than in the case of pure soy lecithin liposomes (cf. Table 3).

Example 7

Preparation of hexachlorophene-containing liposomes by ethanol injection

Dissolve 1.0 g of hexachlorophene, 0.2 g of tocopherol, 2.5 g of soy lecithin and 2.5 g of OHAP in 20 g of ethanol and inject, using a suitable syringe, into 74 ml of citrate/phosphate buffer (pH 5.5; containing 0.2% sorbic acid/potassium sorbate) under ultrasonic treatment. Filter the dispersion through a membrane (0.45 μm). The final concentration is 1% hexachlorophene, 5.0% lipid and 20% ethanol, the vesicle size being 65±11.4 nm. Use this liposome dispersion for preparing a gel with 1 g of polyacrylic acid (Carbopol 984®).

The residual active content after 1-year storage at 4° C. is 99.4%, the vesicle size being only 66.3±10.3 nm.

Example 8

Preparation of OHAP-containing liposomes for the encapsulation of hydrophilic substances by high-pressure homogenization at a 16% OHAP vesicle content Introduce 42 g of soy lecithin and 8 g of OHAP into a round-bottom flask and dissolve in ethanol. Remove the solvent under reduced pressure using a rotary evaporator. Redisperse the resulting film with 450 ml of quinoline yellow-(2 mg/ml) or Na-carboxyfluoresceine- (2 mmolar) containing isotonic phosphate buffer (pH 6.5). Treat the resulting lipid dispersion by means of high-pressure homogenization ($1.1 \cdot 10^8$ Pa; 20 min) and subsequently filter through a membrane (0.45 μm).

The following Table shows the initial vesicle size and encapsulation rate as well as the excellent stability of these two parameters after 1-month storage at 4° C.:

| Encapsulated substance Substance | Vesicle size (nm) | | Encapsulation rate | |
| --- | --- | --- | --- | --- |
| | initial value | after 1 month | initial value | after 1 month |
| Quinoline yellow | 35.6 ± 8.4 | 33.1 ± 8.6 | 3.5% | 3.4% |
| Na-carboxy-fluoresceine | 33.4 ± 8.6 | 33.0 ± 8.7 | 3.0% | 3.1% |

The vesicles were essentially impermeable, as compared with the Handjani's "dysfunctional vesicle permeability" at a FAECH content or "percentage higher than 15%".

*rate=percentage by weight of active ingredient incorporated into the liposomes to total weight.

Example 9

Preparation of a liposomal dispersion containing Lipacide® PCO (20%)

Introduce 3.2 g of soy lecithin and 0.8 g of Lipacide® PCO into a suitable round-bottomed flask and dissolve in ethanol. Remove the solvent under vacuum using a rotary evaporator. While shaking vigorously, redisperse the resulting lipid film with 36 ml of isotonic phosphate buffer having a pH of 6.5 (which contains 1.1% of phenoxyethanol as preservative). Subject the MLV dispersion to high-pressure homogenization ($1.4 \cdot 10^8$ Pa; 25 min) and subsequently filter through a cellulose acetate membrane (pore size 0.45 μm).

Example 10

Preparation of a liposomal dispersion containing Lipacide® DPHP: (20%)

Introduce 12 g of soy lecithin, 3 g of Lipacide® DPHP and 60 mg of butylhydroxy toluene (antioxidant) into a screwable amber glass vessel of appropriate size and dissolve in a mixture of 8.0 g of ethanol and 8.0 g of glycerol while heating (on a water bath). While stirring, add to this homogeneous melt 69 ml of isotonic phosphate buffer having a pH of 6.5 (which optionally contains a water-soluble pharmaceutical or cosmetic agent).

Subject the resulting MLV dispersion to high-pressure homogenization ($1.1 \cdot 10^8$ Pa; 20 min) and subsequently filter through a cellulose acetate membrane (0.45 μm).

Example 11

Preparation of an MHAP-containing liposomal gel: (16%)

Introduce 8.4 g of soy lecithin, 1.6 g of MHAP and 40 mg of butylhydroxy toluene (antioxidant) into a screwable amber glass vessel of appropriate size and dissolve in 10.0 g of ethanol while heating (on a water bath). While stirring, add to the homogenous melt 78.2 ml of phosphate buffer having a pH of 6.5 (which contains 1.1% of phenoxyethanol as preservative). Subject the resulting MLV dispersion to high-pressure homogenization (1.1.108 Pa; 20 min) and subsequently filter through a cellulose acetate membrane (0.45 μm). While stirring, sprinkle 1.75 g of preneutralized polyacrylic acid (PNC®) onto the resulting SUV dispersion. It is recommended that the developing hydrogel be allowed to completely swell overnight by applying low shearing forces.

Example 12

Preparation of a liposomal gel containing Lipacide® C8CO: (16%)

Introduce 3.36 g of soy lecithin into a screwable amber glass vessel of appropriate size and dissolve in a mixture of 3.2 g of ethanol and 3.2 g of glycerol while heating (on a water bath). While stirring, add to the homogenous melt 0.64 g of Lipacide® C8CP and 24.9 ml of phosphate buffer having a pH of 6.5. Subject the resulting MLV dispersion to high-pressure homogenization ($1.4 \cdot 10^8$ Pa; 25 min) and subsequently filter through a cellulose acetate membrane (pore size 0.45 μm). While stirring, add to this SUV dispersion a trituration of 0.7 g of preneutralized polyacrylic acid (PNC®) and 4.0 g of octyldodecyl myristate ODM. It is recommended that the developing hydrogel be allowed to completely swell overnight by applying low shearing forces.

Cosmetic and Pharmaceutical Compositions or Formulations

Innumerable cosmetic and pharmaceutical compositions and preparations, preferably for topical application, embodying liposomes according to the present invention and cosmetically- and/or pharmaceutically-active ingredients, in effective amounts, can be prepared in conventional manner and may incorporate any such active ingredient, preferably but not necessarily a lipid-soluble ingredient, those previously mentioned herein being representative of the active ingredients which may be employed, together with a cosmetically- or pharmaceutically-acceptable carrier or diluent, preferably a topically-acceptable carrier or diluent.

Representative examples of such compositions or preparations follow:

| Composition of a Cosmetic Topical Product | |
|---|---|
| Name of Ingredients | percentage formula (%) |
| Soy lecithin | 10,000 |
| Oleic acid-esterified collagen hydrolysate (OHAP) (representative FAECH) | 10,000 |
| dl-α-Tocopherolnicotinate | 2,000 |
| Butylated Hydroxytoluol (BHT) | 0,008 |
| Ethanol | 15,000 |
| Sodium Phosphate.2H$_2$O | 0,856 |
| Disodium Phosphate.2H$_2$O | 0,634 |
| Hostacerin PN 73 | 1,750 |
| Purified Water | 59,552 |
| Perfume | 0,200 |
| | 100,000 |

Manufacturing Procedure:

In an external container sodium phosphate and disodium phosphate are dissolved in purified water (I).

In an external container placed in a water bath soy lecithin, OHAP, tocopherol nicotinate and BHT are dissolved in ethanol at moderate temperature (II).

(I) is poured into (II) under stirring and the resulting dispersion finally homogenized using a high pressure homogenizer (III).

The gel is produced by sprinkling the Hostacerin onto the stirred liposome dispersion (III) and allowed to swell for 24 hours (IV).

| Stability of lecithin-lipoaminoacid/lipopedtide liposomes | | | |
|---|---|---|---|
| Lipid phase consisting of lecithin and X; the weight ratio lecithin/X is 8:2. X: | | Vesicle size [nm] | Main vesicle size [nm]/percentage |
| Lecithin | Initially | 25.5 ± 5.4 | 25.4 (99.5%) |
| | 4 months/21° C. | 55.0 ± 13.9 | 54.1 (98.9%) |
| OHAP | Initially | 18.4 ± 3.0 | 18.4 (99.8%) |
| | 4 months/21° C. | 18.9 ± 1.8 | 18.9 (100%) |
| Lipacide ™ PCO | Initially | 33.1 ± 8.4 | 32.6 (98.9%) |
| | 4 months/21° C. | 32.5 ± 8.2 | 32.0 (99%) |
| Lipacide ™ DPHP | Initially | 23.0 ± 4.1 | 22.8 (99.5%) |
| | 4 months/21° C. | 24.4 ± 4.3 | 24.3 (99.8%) |
| Lexein ™ A200 (MHAP) | Initially | 28.8 ± 5.1 | 26.7 (99.8%) |
| | 4 months/21° C. | 29.5 ± 7.3 | 29.4 (100%) |

Finally the perfume is mixed under stirring into the liposome gel (IV).

The foregoing cosmetic composition may be topically applied and, when so applied, provides an increased supply of blood and nutriments to the skin, has a positive influence upon skin regeneration, improves the barrier function and moisture content of the skin, and reduces the rate of skin aging.

Composition of a Pharmaceutical Topical Product

| Name of Ingredients | percentage formula (%) |
| --- | --- |
| Soy lecithin | 8,000 |
| Oleic acid-esterified collagen hydrolysate (OHAP) (representative FAECH) | 2,000 |
| Tretinoin | 0,050 |
| Butylated Hydroxytoluol (BHT) | 0,004 |
| Phenoxyethanol | 1,000 |
| Ethanol | 5,000 |
| Sodium Phosphate | 1,120 |
| Disodium Phosphate | 0,830 |
| Tromethamine (USPXXII) (buffer) | 2,800 |
| Carbopol ™ 934 (Polyacrylic acid) | 1,250 |
| Purified Water | 77,946 |
|  | 100,000 |

Manufacturing Procedure:

In an external container sodium phosphate, disodium phosphate and phenoxyethanol are dissolved in purified water (I).

Carbopol™ 934 and tromethamine are mixed, dispersed in 30% (I) and stirred to complete swelling (II).

In an external container soy lecithin and OHAP are dispersed under stirring in the remaining amount of (I). Avoiding exposure to light tretinoin and BHT are dissolved in ethanol and poured into the lecithin/OHAP-dispersion under homogenization with an Ultraturrax™ for 5 min. Finally this dispersion is homogenized using a high pressure homogenisator (III).

(II) and (III) are mixed and stirred until complete swelling (IV). These preparation steps are also carried out under avoidance of light exposure.

The foregoing pharmaceutical composition may be topically applied for the treatment of acne, promotes a homogenous and long-lasting distribution of the drug tretinoin in the skin, and promotes an improved toleration of the tretinoin therapy by the skin.

The liposome compositions of the present invention have the advantage of stability, that is, an important reduced tendency to aggregate and/or to grow in size upon passage of time without an increase in permeability, as shown in the foregoing comparative Examples, especially when the liposome compositions of the invention consist essentially of "SUV", namely, small unilamellar (one bilayer) vesicles, in contrast to usual vesicles of the prior art and those vesicles of the prior art having less than the required amount of the important ingredient fatty acid-esterified collagen hydrolysate, representatively the ingredient OHAP, which impart important characteristics to the vesicles of the present invention, including the aforementioned stability and resistance to growth in size and permeability over a period of time. Such SUV according to the present invention are, as previously disclosed, small unilamellar (one bilayer) vesicles having a particle size between about 20 and 150 nm, preferably between about 20 and 70 nm, and which contain between about 10% and 90%, preferably 16% and 90% percent by weight of fatty acid-esterified collagen hydrolysate, representatively of OHAP, and especially between about 20% and 80% by weight of the aforesaid essential characteristic-enhancing ingredient. Such SUV are representatively produced by the procedure of Examples 1–5, 8, 11, and 12, as shown by freeze-fracture micrographs, whereas the vesicles produced by ethanol injection in Examples 6 and 7 are multilamellar (more than one bilayer). Thus, depending upon the technique employed, the production of unilamellar (SUV) or multilamellar (MLV) vesicles can be selected, and the size of the vesicles can in any case be controlled by variation in the fatty-acid esterified collagen hydrolysate, representatively the OHAP, content of the vesicle membrane. This phenomenon is previously unheard of.

It is accordingly seen from the foregoing that the present invention provides novel liposome compositions consisting essentially of small vesicles, preferably but not limited to unilamellar (one bilayer) vesicles, consisting essentially of lecithin and between about 10 and 90 percent, preferably 16 and 90 percent, by weight of fatty acid-esterified collagen hydrolysate, especially between about 20 and 80 percent, representatively such percentages of OHAP as a representative species of the type of FAECH which may advantageously be employed, and a method for the preparation thereof, as well as the important aspect of vesicle dimensional control and particle size reduction by employing increased ratios of FAECH to lecithin, and further a method for the use thereof in the preparation of cosmetic and pharmaceutical preparations or compositions, and such compositions themselves containing effective amounts of cosmetically-effective or pharmaceutically-effective active ingredients, which are preferably but not necessarily lipid-soluble active ingredients, with all of the attendant advantages as set forth and illustrated in the foregoing, especially the important aspect of stability against undesirable and intolerable size increases in individual vesicle dimensions over time (which shortcoming has characterized previous similar prior art liposome vesicles and compositions containing the same), without an increase in permeability, and consequently an importantly improved storage stability, all of which advantages are attributable to the high percentage of fatty-acid esterified collagen hydrolysate, representatively OHAP, in the vesicle membrane or wall.

It is to be understood that the present invention is not to be limited to the exact details of operation, or to the exact compounds, compositions, methods, procedures, or embodiments shown and described, as various modifications and equivalents will be apparent to one skilled in the art, wherefore the present invention is to be limited only by the full scope which can be legally accorded to the appended claims.

We claim:

1. A liposome preparation wherein the vesicles are impermeable, non-aggregating, and have a dimensionally-stable small particle size of about 20 to 150 nm and a unilamellar vesicle membrane which consists essentially of a mixture of 84 to 10%.by weight of a phosphatidyl choline having a saturated or unsaturated C16–C20 fatty acid chain, and 16 to 90% by weight of a lipoaminoacid or lipopeptide wherein the esterifying fatty acid in the lipoaminoacid or lipopeptide is a C8–C24 carboxylic acid, prepared by dispersing the aforesaid mixture in an aqueous phase at a pH of about 5 to 7 in the presence of a buffer which is effective in this pH range and subjecting the dispersion to high-pressure homogenization or by injecting the aforesaid mixture together with ethanol into an aqueous phase at a pH of about 5 to 7 in the presence of a buffer which is effective in this pH range to form said liposome preparation, said liposomes having incorporated therein a therapeutic or cosmetic agent.

2. A liposome preparation according to claim 1, wherein the vesicle membrane contains 20–80% by weight of lipoaminoacid or lipopeptide.

3. A liposome preparation according to claim 1, wherein the lipoaminoacid or lipopeptide is selected from the group consisting of collagen oleoyltetra- and pentapeptide, caproyl collagen aminoacids, myristoyl hydrolyzed animal protein, dipalmitoyl hydroxy proline, and palmitoyl collagen aminoacids.

4. A liposome preparation according to claim 1, wherein the lipoaminoacid or lipopeptide is collagen oleoyl tetra- and pentapeptide.

5. A liposome preparation according to claim 1, wherein the phosphatidyl choline is in the form of a natural lecithin and the particle size of the vesicles is 20 to 70 nm.

6. A liposome preparation according to claim 4, wherein the phosphatidyl choline is in the form of soy or egg lecithin and the particle size of the vesicles is 20 to 70 nm.

7. A liposome preparation according to claim 2, wherein the lipoaminoacid or lipopeptide is selected from the group consisting of collagen oleoyltetra- and pentapeptide, caproyl collagen aminoacids, myristoyl hydrolyzed animal protein, dipalmitoyl hydroxy proline, and palmitoyl collagen aminoacids.

8. A liposome preparation according to claim 2, wherein the lipoaminoacid or lipopeptide is collagen oleoyl tetra- or pentapeptide.

9. A liposome preparation according to claim 1, wherein the liposomes are dispersed in a gel.

10. A liposome preparation according to claim 9, wherein the gel is selected from the group consisting of a polyacrylic acid, gel a cellulose gel, or a sodium salt of an acrylic acid-acrylamide copolymerisate.

11. A liposome preparation according to claim 1, wherein the therapeutic or cosmetic agent is selected from hexachlorophene, tretinoin, sodium heparin, minocycline, meclocycline, α-tocopherol nicotinate, tromantadine base, croconazole, cyproterone, cyproterone acetate, dexpanthenol, 2-tert.-butyl-4-cyclohexylphenyl nicotinate-N-oxide, ethinyl estradiol, and spironolactone.

12. A liposome preparation according to claim 1, wherein the therapeutic or cosmetic agent is selected from corticosteroids, androgens, non-steroidal antiphlogistics, dihydropyridines, erythromycin esters, local anesthetics, estradiol esters, plant extracts, and antihistaminics.

13. A cosmetic composition suitable for topical application to humans comprising a liposome preparation of claim 1, wherein the liposomes contain a cosmetically- and topically-effective active agent, and a cosmetically-acceptable carrier or diluent.

14. A pharmaceutical composition suitable for topical application to humans comprising a liposome preparation of claim 1, wherein the liposomes contain a pharmaceutically- and topically-effective active agent, and a pharmaceutically-acceptable carrier or diluent.

15. A cosmetic composition of claim 13, wherein the active agent is lipid soluble and is present in the vesicle wall or membrane.

16. A cosmetic composition of claim 13, wherein the active agent is water soluble and is encapsulated within the vesicle walls.

17. A pharmaceutical composition of claim 14, wherein the active agent is lipid soluble and is present in the vesicle wall or membrane.

18. A pharmaceutical composition of claim 14, wherein the active agent is water soluble and is encapsulated within the vesicle walls.

* * * * *

UNITED STATES PATENT AND TRADEMARK OFFICE
CERTIFICATE OF CORRECTION

PATENT NO. : 5,498,420

DATED : March 12, 1996

INVENTOR(S) : Edgar Mentrup, Christoph Michel and Thomas Purmann

It is certified that error appears in the above-indentified patent and that said Letters Patent is hereby corrected as shown below:

Title Page, [19], line 2: "Mentrup Edgar et al." should read -- Edgar Mentrup et al. --. PTO Title Page, [75], "Mentrup Edgar" should read -- Edgar Mentrup --.

Column 8, line 58: "Group" should read -- group --.

Column 18, line 11: "(1.1.108 Pa;" should read -- $(1.1.10^8$ Pa; --.

Column 21, line 17: "(1.1.108 Pa;" should read -- $(1.1.10^8$ Pa; --.

Column 21, line 43: "lipopedtide" should read -- lipopeptide --.

UNITED STATES PATENT AND TRADEMARK OFFICE
CERTIFICATE OF CORRECTION

PATENT NO. : 5,498,420
DATED : March 12, 1996
INVENTOR(S) : Edgar Mentrup, Christoph Michel and Thomas Purmann It is certified that error appears in the above-indentified patent and that said Letters Patent is hereby corrected as shown below:

Column 25, line 8: "and" should read -- or --.
　　See page 2 of R&A dtd July 7, 1995, <u>Claim 5, line 3</u>.
Column 25, line 29: "acid, gel" should read
　　-- acid gel, --. Pg. 2 of R&A dated July 22, 1994, <u>Claim 11, Line 3</u>.

Signed and Sealed this

Eleventh Day of June, 1996

Attest:

BRUCE LEHMAN

Attesting Officer　　　Commissioner of Patents and Trademarks